(12) United States Patent  (10) Patent No.: US 8,843,852 B2
Berry et al.  (45) Date of Patent: Sep. 23, 2014

(54) MEDICAL INTERFACE, ANNOTATION AND COMMUNICATION SYSTEMS

(75) Inventors: Matthew M. Berry, Highland, UT (US); Robert M. Berry, Highland, UT (US); Wesley D. Chapman, Draper, UT (US); Shawn B. Saunders, Highland, UT (US); Michael V. Caldwell, Provo, UT (US); Spencer T. Hall, Provo, UT (US); Christopher T. Owens, Provo, UT (US); Daniel D. Lyman, Provo, UT (US); Darren L. Turetzky, Orem, UT (US)

(73) Assignee: Orca Health, Inc., Sandy, UT (US)

( * ) Notice: Subject to any disclaimer, the term of this patent is extended or adjusted under 35 U.S.C. 154(b) by 455 days.

(21) Appl. No.: 13/093,272

(22) Filed: Apr. 25, 2011

(65) Prior Publication Data

US 2012/0159391 A1   Jun. 21, 2012

Related U.S. Application Data

(60) Provisional application No. 61/424,548, filed on Dec. 17, 2010, provisional application No. 61/442,686, filed on Feb. 14, 2011, provisional application No. 61/442,666, filed on Feb. 14, 2011.

(51) Int. Cl.
    *G06F 3/048*   (2013.01)
    *A61B 5/00*    (2006.01)
    *G06F 17/24*   (2006.01)

(52) U.S. Cl.
    CPC ....... *A61B 5/4824* (2013.01); *A61B 2560/0295* (2013.01); *G06F 17/241* (2013.01); *A61B 5/748* (2013.01)
    USPC .......................................... 715/823

(58) Field of Classification Search
    CPC ...................................... G06F 17/241
    USPC .................................. 715/821–823
    See application file for complete search history.

(56) References Cited

U.S. PATENT DOCUMENTS

| 2005/0104896 | A1* | 5/2005 | Kerr et al. ............ 345/619 |
| 2007/0242069 | A1* | 10/2007 | Matsue et al. .......... 345/428 |
| 2008/0027917 | A1* | 1/2008 | Mukherjee et al. ......... 707/3 |
| 2011/0145693 | A1* | 6/2011 | Mutic et al. .......... 715/233 |

* cited by examiner

*Primary Examiner* — Enrique Iturralde
(74) *Attorney, Agent, or Firm* — Workman Nydegger

(57) ABSTRACT

In one aspect, annotating graphical elements can include displaying a graphical element at a user interface which provides annotation options for selecting areas for annotation, and options for adding highlighting and comments. A user uses the annotation options to select areas of the graphical element for annotation, to select highlighting and user input methods, to and provide comments. After receiving the user input, the graphical elements can be displayed along with the selected annotations. In another aspect, providing information about medical conditions can include presenting a user interface that includes a representation of an anatomical region of the human body. A user can use user-selectable display elements to indicate areas in the anatomical region in which a medical condition is experienced. After receiving the user input, the user can be presented with a selection of medical conditions corresponding to the selected areas, as well as information about medical specialists.

20 Claims, 11 Drawing Sheets

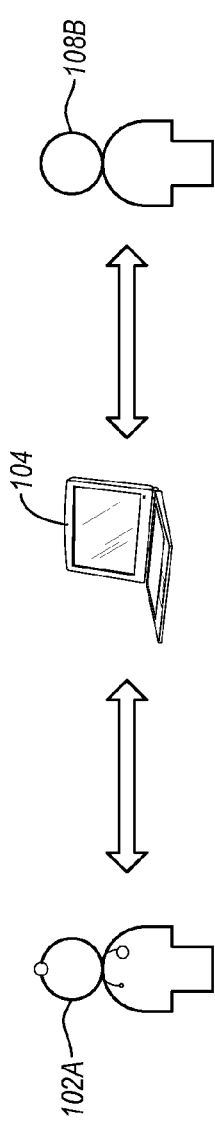
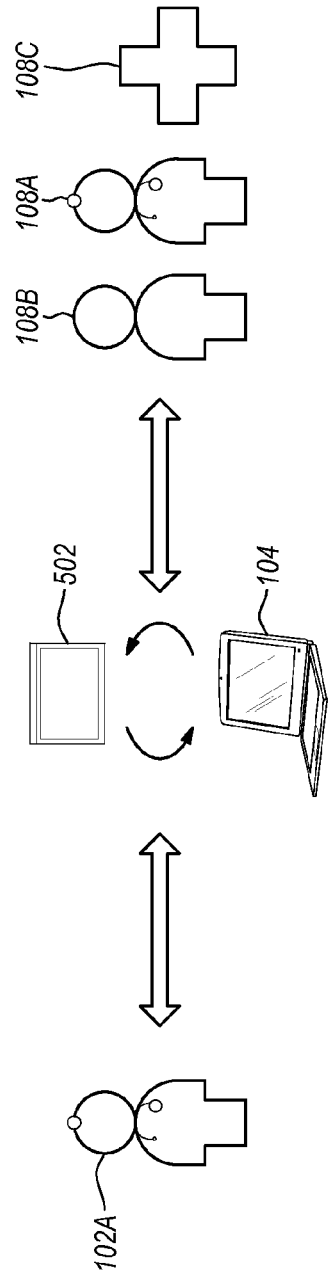

MEDICAL INTERFACE, ANNOTATION AND COMMUNICATION SYSTEMS

CROSS-REFERENCE TO RELATED APPLICATIONS

This application claims the benefit of, and priority to the following three provisional applications: U.S. Provisional Application No. 61/424,548 filed Dec. 17, 2010, entitled "INTERACTIVE ANATOMICAL MEDICAL APPLICATION USER INTERFACES;" U.S. Provisional Application No. 61/442,686 filed Feb. 14, 2011, entitled "INTERACTIVE ANATOMICAL MEDICAL APPLICATION USER INTERFACES;" and U.S. Provisional Application No. 61/442,666 filed Feb. 14, 2011, entitled "INTERACTIVE GRAPHICAL ELEMENT ANNOTATION." Each of these applications are incorporated by reference in their entireties.

BACKGROUND

1. The Field of the Invention

This invention relates to systems, methods, and computer program products related to the interactive annotation of displayed graphical elements and to providing users with information about selected graphical elements.

2. The Relevant Technology

Annotation typically involves appending descriptive information to objects. In a simple form, for example, annotation may involve the addition of handwritten notes on paper documents. Thus, annotation can involve appending handwritten notes, markings, etc. to content of the paper documents.

With the development of computing technology, annotation has been extended to electronic forms as well. For example, some office suites (e.g. Microsoft® Office®) enable electronic annotations to be added to documents through the use of notes, revision tools, etc. Furthermore, some ability exists to add annotations to graphical elements, such as through the use of image editing suites (e.g., Adobe® Photoshop®). Thus, some ability exits to perform electronic annotation using generic tools such as office suites and image editing suits.

Despite the foregoing, there is an ongoing need to improve and ease the ability to electronically annotate graphical elements (e.g., images, video, etc), and to share these annotations with others.

BRIEF SUMMARY

Implementations of the present invention include systems, methods and computer program products configured for annotating and sharing graphical elements, as well as for providing information surrounding selected graphical elements. In one or more embodiments, an annotation computing provides one or more interactive user interfaces for managing, viewing, displaying, manipulating, and/or annotating the graphical elements. One or more embodiments also provide a central clearinghouse for obtaining, storing, tracking, and sharing information, including annotated and/or un-annotated graphical elements. Further, in the context of medical annotation, some embodiments can extend to receiving information about experienced medical conditions and to providing medical information or advice about the inputted condition(s).

For example, a method for annotating graphical elements can include displaying graphical element(s) with a user interface and providing annotation options for selecting areas of the graphical element(s) for annotation. After a user selects area(s) of the graphical element(s) for annotation, an annotation dialogue can be provided which contains annotation options for annotating the selected area(s). The annotation options can include highlighting options and comment input options. Annotations can also comprise audible as well as visual/textual annotations. Embodiments of the invention can also include receiving user input selecting highlighting options and comment input options, and receiving user comment input. After receiving the user input, the graphical element(s) can be displayed with the annotation(s) and/or selectable options for accessing the annotation(s).

In addition, a method for providing information about a medical condition based on user input can include presenting a user with a user interface that in includes an anatomical subassembly representing an anatomical region of the human body. The user interface can also include user-selectable display elements which, when selected, indicate areas in the anatomical subassembly corresponding to areas in which a medical condition is experienced. User input selecting one or more of the user-selectable elements of the anatomical assembly can be received. In response, the user can be presented with a selection of medical conditions corresponding to the selected elements. In addition, the user can be presented with information about one or more medical specialists knowledgeable about the medical conditions and the selected elements.

This Summary is not intended to identify key features or essential features of the claimed subject matter, nor is it intended to be used as an aid in determining the scope of the claimed subject matter.

Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims, or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5A illustrates a flow diagram of communication paths within an annotation environment, in accordance with one or more implementations of the invention;

FIG. 5B illustrates a flow diagram of communication paths within an annotation environment, in accordance with one or more implementations of the invention;

DETAILED DESCRIPTION

Embodiments of the present invention may comprise or utilize a special purpose or general-purpose computer including computer hardware, as discussed in greater detail below.

Embodiments described herein are generally directed to methods, systems, and computer storage media configured for annotating graphical elements, which can include images, videos, models, and the like. Embodiments of the invention can also include accessing and transmitting the annotations.

In one or more embodiments, an annotation computing system receives, generates, or obtains one or more graphical elements and provides one or more interactive user interfaces for managing, viewing/displaying, manipulating, and/or annotating the graphical elements. Graphical element manipulation includes any form of image or video manipulation, such as rotating, zooming, color modification and/or adjustment, cropping, trimming, joining, and the like. Graphical element annotation includes any form of descriptive commenting or enhancement to graphical elements, such as the addition of one or more highlights, selections, shapes, objects, textual comments, visual or audible enhancements, etc.

In some embodiments, audible annotations can also be applied to and associated with the graphical elements.

Embodiments also include a central clearinghouse system for obtaining, storing, tracking, and sharing information, including annotated and/or un-annotated graphical elements. A clearinghouse can connect the annotation computing system with third-party sources and destinations of information, other annotation computing systems, or other clearinghouses. At least one embodiment also includes sharing and obtaining graphical elements separate from any clearinghouse(s).

As a preliminary matter, one will appreciate that the embodiments described herein can be applied broadly to any field in which the annotation of graphical elements is desirable or useful (e.g. mechanical arts, medicine, business methods, chemical arts, entertainment, etc.). Nevertheless, for purposes of convenience in description, the following text and figures describe the inventive embodiments primarily with respect to a system and graphical user interface for annotating medical graphical elements, such as, but not limited to human anatomical features.

In the context of medical annotation, some embodiments can extend to methods, systems, and computer storage media for inputting information about experienced medical conditions (e.g., experience pain), and receiving medical information or advice about the inputted condition. These embodiments can extend to local or remote diagnosis, education, and investigation about medical conditions, tracking medical histories, etc. These embodiments can be employed separately from or in connection with the annotation computing system and the clearinghouse.

Figure 1:
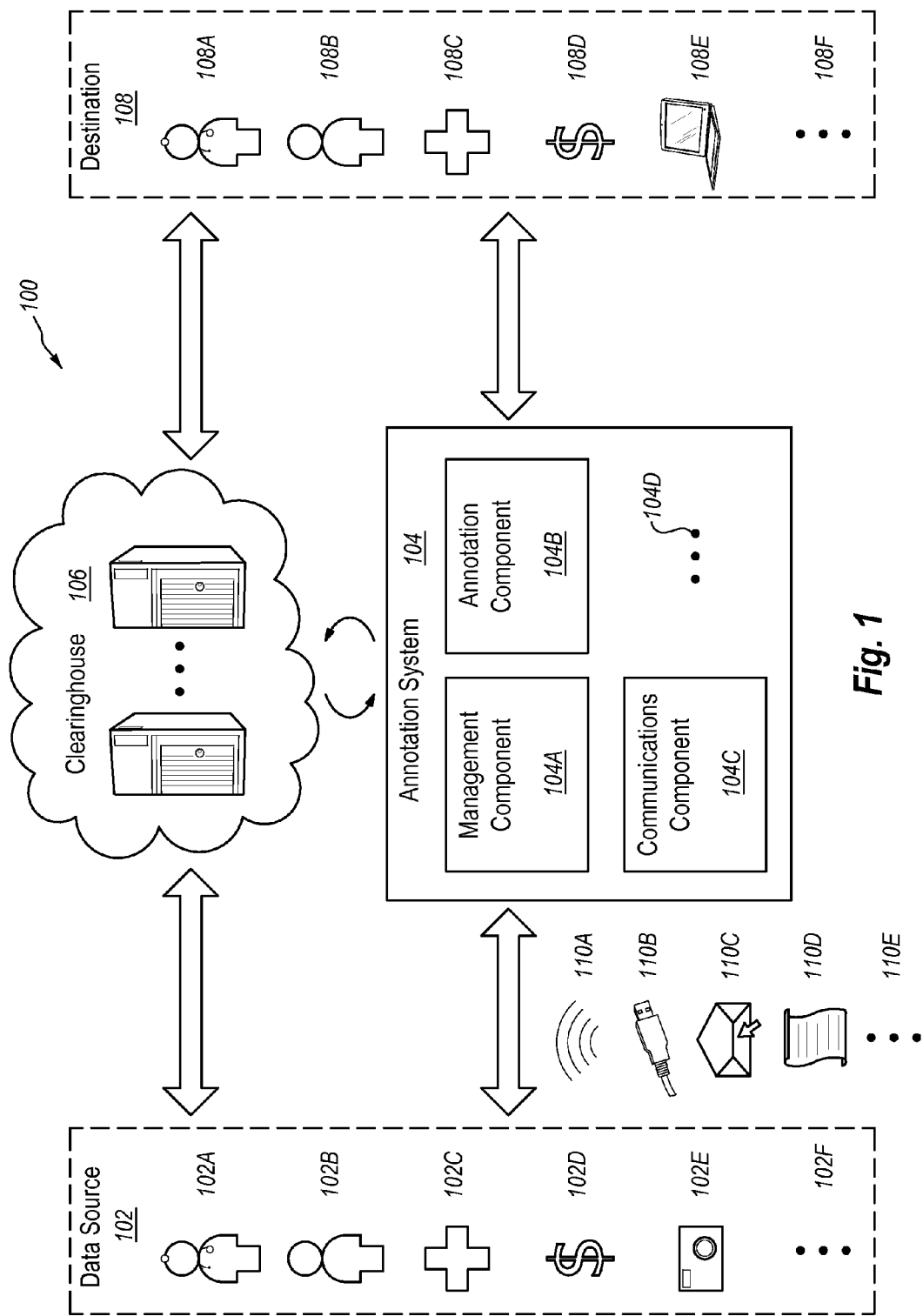
FIG. 1 illustrates a schematic diagram of an annotation environment for annotating and sharing records in accordance with one or more implementations of the invention.

FIG. 1 illustrates a schematic diagram of an annotation environment 100 for annotating and sharing records, including graphical elements, in accordance with one or more implementations of the invention. The annotation environment 100 can include an annotation system 104 communicatively coupled with one or more data sources 102 and one or more data destinations 108. The annotation environment 100 can also include the annotation system 104 communicatively coupled with and a central record clearinghouse 106, which can, in turn, be coupled with the data source(s) 102 and destination(s) 108. If used, the clearinghouse 106 can serve as a central repository for storing and tracking records and for communicating records between the annotation system 104, the data source(s) 102, and the destination(s) 108.

The annotation system 104 can comprise any computing system capable of receiving, sending, and managing records, as well as annotating graphical elements. The annotation system 104 may take the form of a desktop or laptop computer, a personal desktop assistant (PDA), a tablet computer (e.g., iPad), a phone device or other smart device, etc. The annotation system 104 can include a management component 104A, an annotation component 104B, and a communications component 104C. The annotation system 104 can also include any additional components 104D. It will be appreciated that the annotations system 104 can consist of a standalone server system or can comprise a distributed system, such as can be distributed throughout a computing cloud.

The management component 104A can manage one or more textual, graphical and/or audible records. In some embodiments, a record, which can apply to any contextual topic, will include one or more graphical elements. As mentioned previously, the annotation environment 100 can, in one or more implementations, comprise a medical annotation environment. In this environment, each record may be a different medical record for different patients, and each medical record may include one or more graphical elements (e.g., medical images). Alternatively, each medical record may correspond with a different condition connected with the patient, a different doctor visit by the patient, different categories of disease, etc. Of course, a record may simply be the graphical element itself.

The graphical elements can be any appropriate graphical elements including images, videos, and models. For instance, when the annotation system 104 operates in a medical annotation environment, the graphical elements can include images, videos, or models of human or animal anatomical features. Thus, the graphical elements may be virtual anatomical models, Magnetic Resonance Imaging (MRI) scans, X-Ray images, Computerized Axial Tomography (CT or CAT) scans, photographs, endoscopic images or videos, etc. Of course, in other contexts, the graphical elements will correspond directly to the applicable industry. For instance, in the engineering industry, the graphical elements may be engineering schematics, design photographs, artwork, etc.

Whatever forms the records and the graphical elements take, the management component 104A can organize the records into one or more categories. In the medical context, for example, categories may include patients, doctors, medical conditions, hospitals or offices, severity levels, time periods, etc. The management component 104A can also provide functionality for adding or removing categories, adding or removing records or graphical elements, selecting one or more categories or records view viewing or editing, selecting one or more graphical elements for annotation, etc. As discussed more fully herein after, the management component 104A can also provide functionality for sending or receiving records or graphical elements via the communications component 104C.

Figure 2:
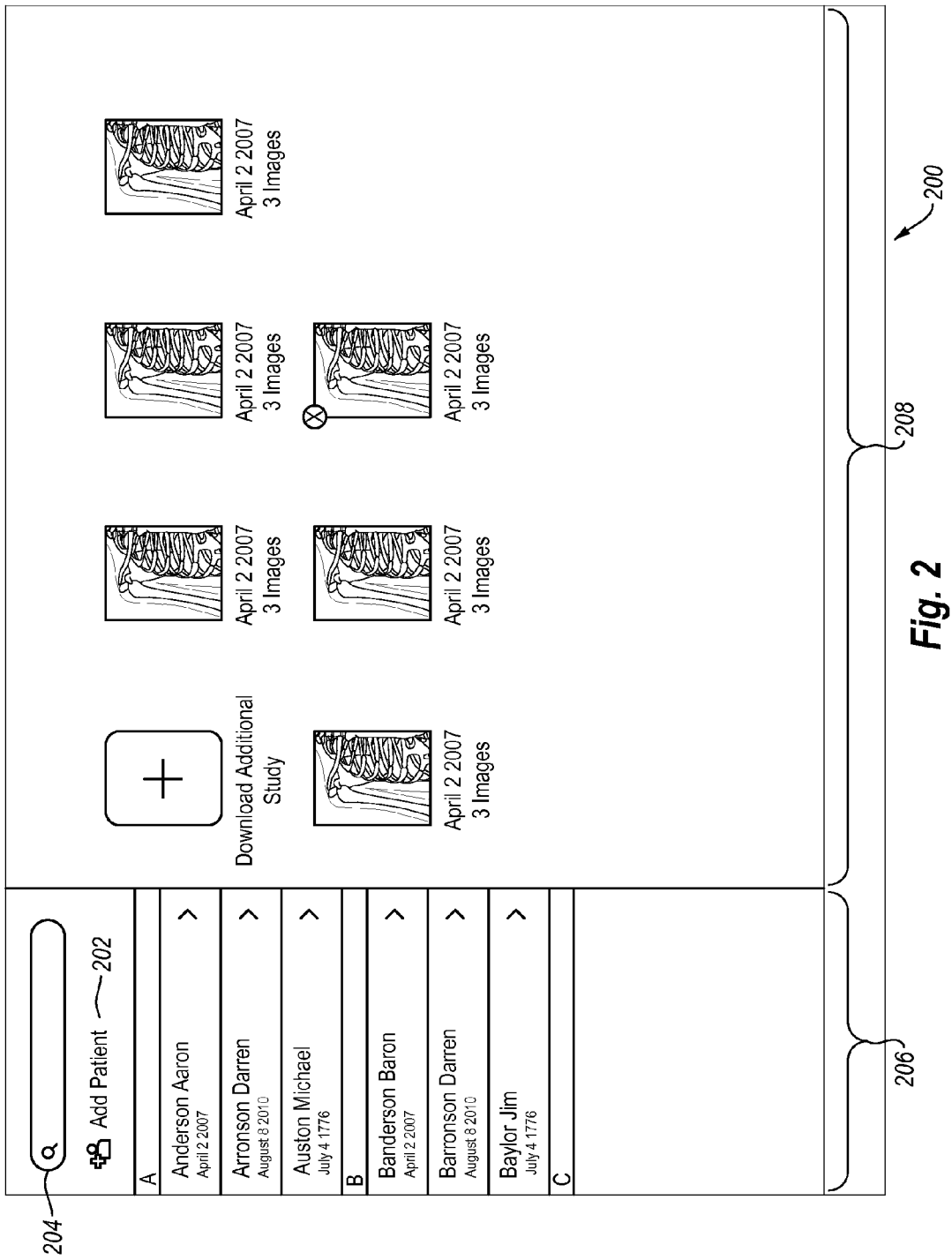
FIG. 2 illustrates a layout of a management user interface of an annotation system, in accordance with one or more implementations of the invention.

For example, FIG. 2 illustrates a layout of a management user interface 200 of the annotation system 104, for managing medical records, consistent with to one or more implementations. The management user interface 200 can include one or more interface controls 202 for adding categories and/or records. As illustrated, each category may correspond to a different patient, and each record may correspond to one or more graphical elements. However, other combinations are also possible. For instance, medical record information can be stored and associated with different owners, different medical professionals, different conditions, etc. Various property information and schemas can be used to group medical records or other medical or graphical information according to any desired need or preference.

The management user interface 200 can also include one or more interface controls 204 for searching existing categories and/or records. Additionally, the management user interface 200 can include a listing 206 of existing categories or records. As illustrated, the listing 206 can be an alphabetical listing of patents. However, any format of the listing 206 is available, such as drop-down menus, tables, combo boxes, etc. In connection with the listing 206 of categories or records, the management user interface 200 can also include a detailed view 208 of graphical elements or a display frame for displaying any combination of graphical elements available in a selected category or record. The graphical elements can be collated, grouped, and displayed in any desired format. The graphical elements can also comprise selectable links to other types of records, such as sound recordings or multimedia files, for example.

The management user interface 200 can be used to access, display, and annotate the graphical elements, or the linked to files (e.g., sound files, multimedia files, etc.).

In one embodiment, the management user interface 200 provides a doctor with a listing of medical records for his or her patients, including records associated with Aaron Anderson, who has been selected. Graphical elements, or any other elements relevant to Aaron Anderson, are shown. The graphical elements can be grouped or categorized, such as by type, a date on which the graphical elements were generated or modified, a date on which the graphical elements were obtained by the annotation system 104, a body part, or according to any other desired characterization. The grouping can be performed automatically, when received, such as by parsing data on the records, or manually, as desired.

The management user interface 200 can also include one or more interface controls for obtaining additional records and/or graphical elements, and one or more interface controls for removing records and/or graphical elements. Additionally, the management user interface 200 can provide one or more interface controls for selecting a graphical element for making, editing, and/or accessing annotations. Further, the management user interface 200 can provide one or more interface controls for sending graphical elements to a destination 108 (e.g., patients, doctors, dentists, clearinghouses, or any other appropriate entity).

The annotation component 104B of the annotation system 104 can provide one or more user interfaces and/or controls for annotating graphical elements. Annotations can include any combination of colors, highlights, animations, images, audio, video, text, and the like, which is added to a record or an element of the record and which is thereafter associated with the record/record element. The annotative elements can be applied from a library of available elements, or can be applied in a free-form manner (e.g. dynamic color selectors, image import, free-hand drawing). In some embodiments, pre-built or pre-scripted annotations are presented for selection and annotation of a graphical element.

Each annotation can also include descriptive comments or other information added by the annotator. Descriptive comments can include text, drawings, images, audio recordings, video recordings, and the like. In some instances, the annotation component 104B can apply optical character recognition or handwriting recognition technology to produce textual output from image or video data. Furthermore, the annotation component 104B can also apply text-to-speech or speech-to-text technology to produce audible output from textual data or to transcribe audible data to textual data. Thus, when annotations include textual, audio, or audio/visual comments and/or descriptions, the annotation system 104 may permit the automatic and dynamic conversion of these items (e.g., text can be dynamically converted to audio, and audio can be dynamically transcribed to text).

The annotations can be visibly presented next to the corresponding element(s) that are annotated. This can also include presenting an annotation symbol comprising a selectable link to audio, textual, or graphical annotations. The symbol or link can be presented as text or image data that is colored, sized, or presented in a distinguishing way and that, when selected, accesses or provides access to the annotation(s).

In one or more implementations, when the annotation environment 100 is used in the medical context, the graphical elements can comprise anatomical features (e.g., images, videos, anatomical models). Thus, the annotations can be applied to highlight one or more injuries or conditions, to indicate the severity of injury, to illustrate treatment options, to indicate healing or degenerative progress over time, to illustrate medical procedures, to indicate medication options, and the like. For example, different shapes can illustrate different types of injuries or conditions, while different colors can represent different severity levels (or vice-versa). In such embodiments, the annotation can include modifying a display characteristic of a graphical element that was already included as part of the record, such as by enhancing coloring, contrast or other display characteristics.

Unique combinations of colors/shapes/objects can be used to indicate different types of annotations, different authors, different conditions, or any combination of differences in annotations. Of course, the annotations (as well as the display characteristics of the annotations) may also be applied merely for teaching or instructive purposes.

In one illustrative example, a doctor may use the annotation system to track the treatment of a patient. With each visit, the doctor can capture a graphical representation of the patient's injury or condition, and make one or more annotations highlighting the healing or degenerative process. Thus, when taken together, the annotated graphical images represent a comprehensive temporal visual history of the treatment process, complete with targeted and appropriate comments in the form of annotations. Graphical representations of the annotations (with or without corresponding symbols) can reflect different stages or diagnosis. This history may be useful to the doctor, other doctors, the patient, insurance carriers, educators, etc. Additionally or alternatively, the patient can send graphical images to the doctor (e.g., between physical visits) so that the doctor can track progress and make detailed recommendations. These recommendations can be communicated back to the patient, at least in part, via annotations made to or with the graphical images.

The annotation component 104B can also provide one or more user interfaces and/or controls for interactively manipulating the graphical elements prior to, during, or after annotation. For example, the annotation component 104B can include tools for rotating, zooming, color adjustment, cropping, trimming, joining, and the like. Furthermore, the annotation component 104B can provide rich interactive features, including the ability to rotate the graphical elements in up to 360°, the ability to apply motion to the graphical elements, the ability to display annotations or animations, etc. This interactively is illustrated in greater detail in subsequent Figures.

One will appreciate, in view of the disclosure herein, that the annotation component 104B can display and annotate both two-dimensional (2D) graphical elements and three-dimensional (3D) graphical elements. Furthermore, the annotation component 104B can convert 2D graphical elements to 3D graphical elements, and vice-versa. For example, the annotation component 104B can convert 2D graphical element to three dimensions by using automatic algorithms, user input, model information, etc. Additionally, the annotation component 104B can convert a 3D graphical element to two dimensions via flattening, cross-sectioning, etc.

When applied to 3D graphical elements, annotations may be visible only when the annotation rotated into view. Alternatively, annotations may be made visible through a visual cue that becomes more prominent as the annotation is rotated into view. Of course, annotations may also be permanently visible regardless of the current view. Similarly, when applied video graphical elements, annotations may only be visible during temporal periods in which the annotation was applied, or may be permanently visible or accessible through bookmarks, time stamps, etc. Annotations can also be selectively displayed in response to receiving predetermined input, such as, but not limited to authorization information, query information and so forth.

Figure 3:
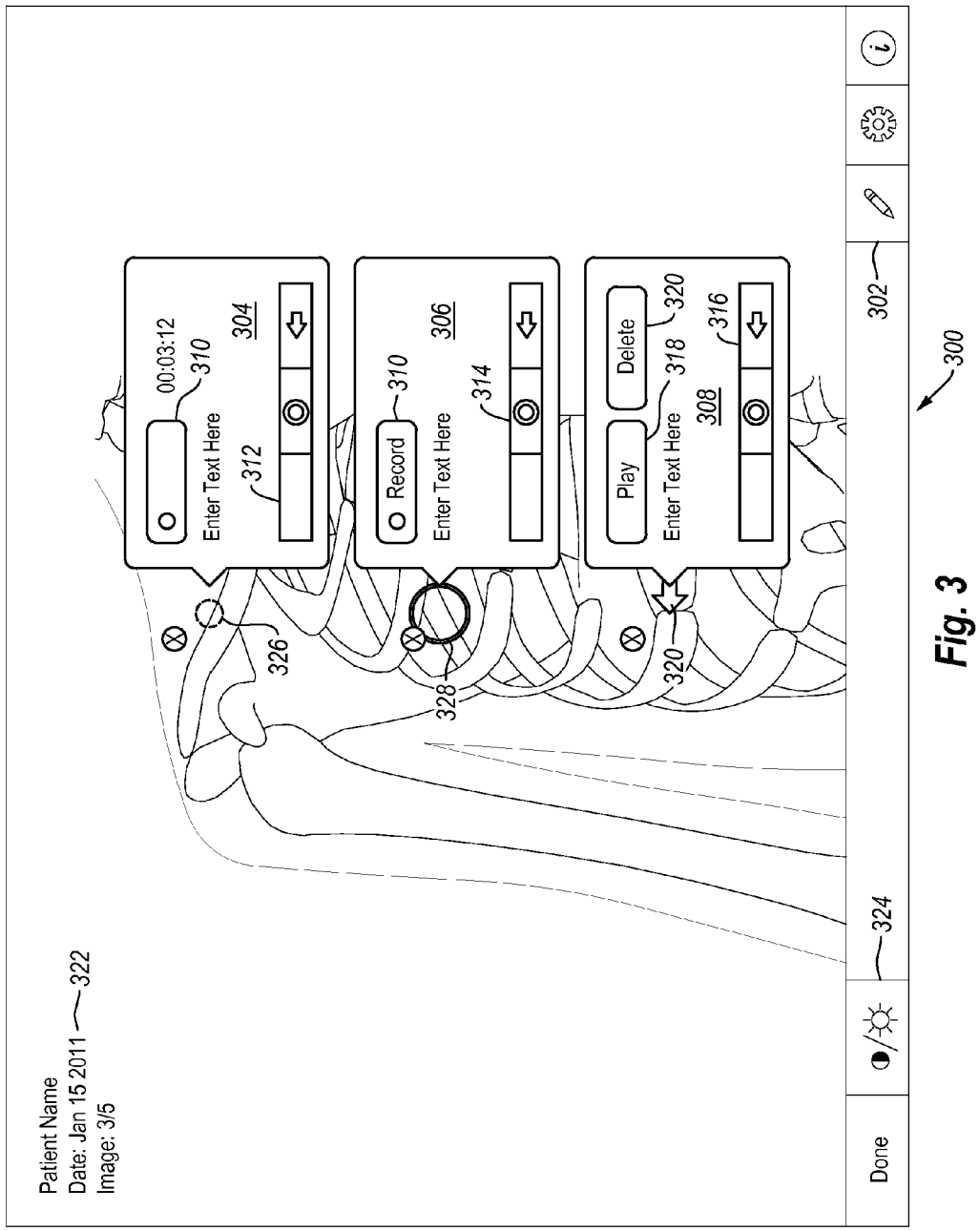
FIG. 3 illustrates a layout of an annotation user interface of an annotation system, in accordance with one or more implementations of the invention.

FIG. 3 illustrates one embodiment of an annotation user interface 300 layout that can be utilized by the annotation system 104. As illustrated, the annotation user interface 300 can display one or more graphical elements, which in this circumstance comprise the image of the skeletal anatomy of a human shoulder. The annotation user interface 300 also provides one or more annotation interface controls 302 for annotating the image, configuring the annotation user interface 300, etc.

Upon selection of an appropriate annotation interface control 302, the user interface 300 can present one or more annotation dialogue 304, 306, 308, along with any appropriate annotation options. In one or more implementations, the annotation dialogue (304, 306, 308) may appear after selection of one or more areas of the graphical element. For example, an annotation dialogue (304, 306, 308) may appear after a user clicks, touches, or otherwise selects a point or region of the graphical element, with the annotation applying to the selected element. The user can customize the annotation in any appropriate manner using the annotation options associated with the annotation dialogue (304, 306, 308). Of course the annotation user interface 300 can also include annotation options that are separate from an annotation dialogue.

In one or more implementations, the annotation options can include selection from among of dots, circles, arrows, text input, audio recording, audio playback, etc. that are to be applied to a point or region of the graphical element (i.e., the image of the shoulder). Of course, the annotation options are not limited to those shown. For instance, the annotation options can also include options to add (or remove) one or more colors, to add (or remove) a plurality of shapes or graphical objects (e.g., polygons, arrows, bullets, stars, numbers), to add (or remove) animations or images, etc.

Annotation dialogue 304 includes several annotation options, such as an annotation option 310 for recording audio or video (shown here as selected and currently recording). In addition, annotation dialogue 304 shows that an annotation option 312 for no highlighting has been selected. Thus, while an area 326 of the shoulder is being annotated, there is no particular highlighting associated with the selected area.

In annotation dialogue 306 the annotation option 310 for recording audio has not been selected. In addition, an annotation option 314 for selecting a circle has been selected. Correspondingly, a circular highlight 328 is displayed on the shoulder corresponding to the area of annotation. Of course, selecting the annotation option 314 may also present additional menus for selecting alternate shapes, colors, sizes, transparency, etc.

Annotation dialogue 308 shows that an annotation option 316 has for selecting a pointer has been selected. Correspondingly, an arrow 320 is displayed on the shoulder which points to the selected area of annotation. Like annotation option 314, additional menus may be used to select a particular pointer type, color, size, shape, transparency, etc. In addition, annotation dialogue 308 shows that media (e.g., audio or video) has been recorded, which is associated with element 320, and that the media can be played back or deleted using the corresponding controls (318 and 320) and interface menus.

Of course, the illustrated annotation dialogues 304, 306, 308 are exemplary only and are not limiting to the annotations dialogues available to the present invention.

The annotation user interface 300 can also display relevant identifying information 322 for the graphical element. For example, when the graphical element is a medical image, the identifying information 322 can include a patient's name, a date (e.g., the date when the graphical element was generated, or the date when the annotation system 104 received the graphical element), and an image identifier, etc. In some embodiments, the identifying information 322 can be part of the graphical element itself, and can used as the basis of gathering additional information about the graphical element (e.g., through the use of optical character recognition technology).

The annotation user interface 300 can also provide a plurality of user interface controls for manipulating the graphical element. For instance, FIG. 3 illustrates that the annotation user interface 300 can include a brightness/contrast selector 324 that provides one or more user interface controls for adjusting the brightness and contrast of the image of the graphical element.

As mentioned previously, any number of manipulation controls can be provided for manipulating graphical elements (including size, shape, brightness, contrast, animations, etc.), whether they be image, video, or otherwise. Such manipulation controls can include user interface controls for cropping, rotating, trimming, joining, etc. Additionally, as discussed previously, annotation user interface can provide any number of interactivity controls that provide rich user interaction with the graphical element. These can controls can include as one or more user interface controls for rotating the graphical element in up to 360°, zooming, rendering motion to the graphical element, converting the graphical element from three-dimensions to two-dimensions (and vice-versa), etc.

Returning again to FIG. 1, the communications component 104C of the annotation system 104 can receive records and graphical elements from the data source(s) 102 (either directly, or via the clearinghouse 106) and can send records and graphical elements to the clearinghouse 106 and/or to the destination(s) 108. The communications component 104C can communicate directly with the data source(s) 102 and the destination(s) 108, or can communicate indirectly (e.g., via the clearinghouse 106). Of course, the communications component 104C may comprise a plurality of components, such as one for receiving data and one for sending data.

As illustrated, communications within the annotation environment 100 can occur over any appropriate connections, such as wireless connections 110A (e.g., WiFi, Bluetooth, infra-red), or wired connections 110B (e.g., network, USB, FireWire, internal bus). It will be appreciated that connections can be made directly (e.g., via a USB connection between the data source 102 and the annotation system 104), or indirectly (e.g., when communications occur over a local or wide area network, or when communications occur via the clearinghouse 106). Regardless of the connection type, communications protocols can also take a variety of forms, such as electronic messages 110C or any other communications protocols 110D. As indicated by the vertical ellipses 110E, any other appropriate connection types and communications protocols are available within the annotation environment 100. For example, one or more implementations may use facsimile, SMS, MMS, and so forth.

The data source(s) 102 should be construed broadly to include any appropriate source(s) of records and/or graphical elements. In the case of a medical annotation environment, for example, graphical elements can originate from one or more doctors 102A (e.g., family practice doctors, radiologists, emergency care doctors, physical therapists, dentists, veterinarians), one or more patients 102B, one or more hospitals 102C, or one or more insurance providers 102D. The graphical elements can also originate from and be automatically attached to a record by the annotation system 104 (e.g., from a still camera or a video camera 102E, a motion capture device, or any other acquisition device at the annotation system 104, or from a direct upload to the annotation system 104, in combination with system logic and tagging mechanisms). In some instances, the data source 102 is separate from other illustrated components, such as the annotation system 104 and the clearinghouse 106, while in other instances the data source 102 is the same as or part of the other illustrated components. Different graphical display characteristics (e.g., size, color, shape, transparency, etc.) can be applied to the different annotations to visually represent the source of the annotations.

As indicated by the vertical ellipses 102F of FIG. 1, the data source 102 can include any number of additional sources of data for records that can be annotated or from which annotations can be derived. For example, the annotation system 104 can also import information (e.g., patient contact information) automatically from one or more external databases. The annotation system 104 can also use internal sources. For instance, in one or more implementations, the annotation system 104 obtains at least some information using optical character recognition of information included in the graphical elements (e.g., identifying information 306).

The annotation system 104 can also utilize speech recognition and/or handwriting recognition. It will be appreciated that in addition to images originating from imaging devices (e.g., cameras, medical imaging devices, etc.), the graphical elements can be partially or entirely virtual (e.g., computer models). Additionally, graphical elements can incorporate, at least in part, motion capture data, metadata, audio data, etc.

The destination(s) 108 should also be construed broadly to include any appropriate destination of records and/or graphical elements. For example records and/or graphical elements can be sent to one or more doctors 108A, one or more patients 108B, one or more hospitals 108C, one or more insurance carriers 108D, or even other annotation systems 108E. Of course, as indicated by the vertical ellipses 108F, other destinations or combinations of destinations are also possible. In many instances, the data source 102 and the destination 108 may be the same.

A patient 102B may send graphical element(s) to an annotation system 104 operated by his or her doctor. After receiving the graphical element(s), the doctor can annotate the graphical elements(s) and send the annotated graphical element(s) back to the patient 108B and/or to another doctor 108A. Thus, patients can be provided access to records associated with their own medical history and/or their family members' medical histories. Of course, the foregoing example is only one possibility. For instance, a doctor 102A (e.g., a radiologist) can send a patient's x-ray the annotation system 104 where the radiologist can apply one or more annotations. The radiologist can subsequently send the annotated x-ray to any appropriate destination 108 (e.g., a family doctor 108A, the patient 108B, a hospital 108C). In another example, medical records are made available insurance entities corresponding to carriers of insurance policies. This way an insurance representative can access and view corresponding medical records and related data for the various carriers. In educational settings, students or professors can be provided access to historical medical records. The various medical records can be annotated and stored with the medical annotations for review and later access according to the invention.

In other embodiments, the medical records and annotations are stored separately, but remain linked by data maintained at the annotation system. When the record is subsequently accessed or transmitted, the record is sent with the appropriate annotations that are relevant and/or authorized for each corresponding recipient. Alternatively, all annotations are included with the medical record and filtering is applied at the recipient system(s) to display only authorized annotations.

Figure 4:
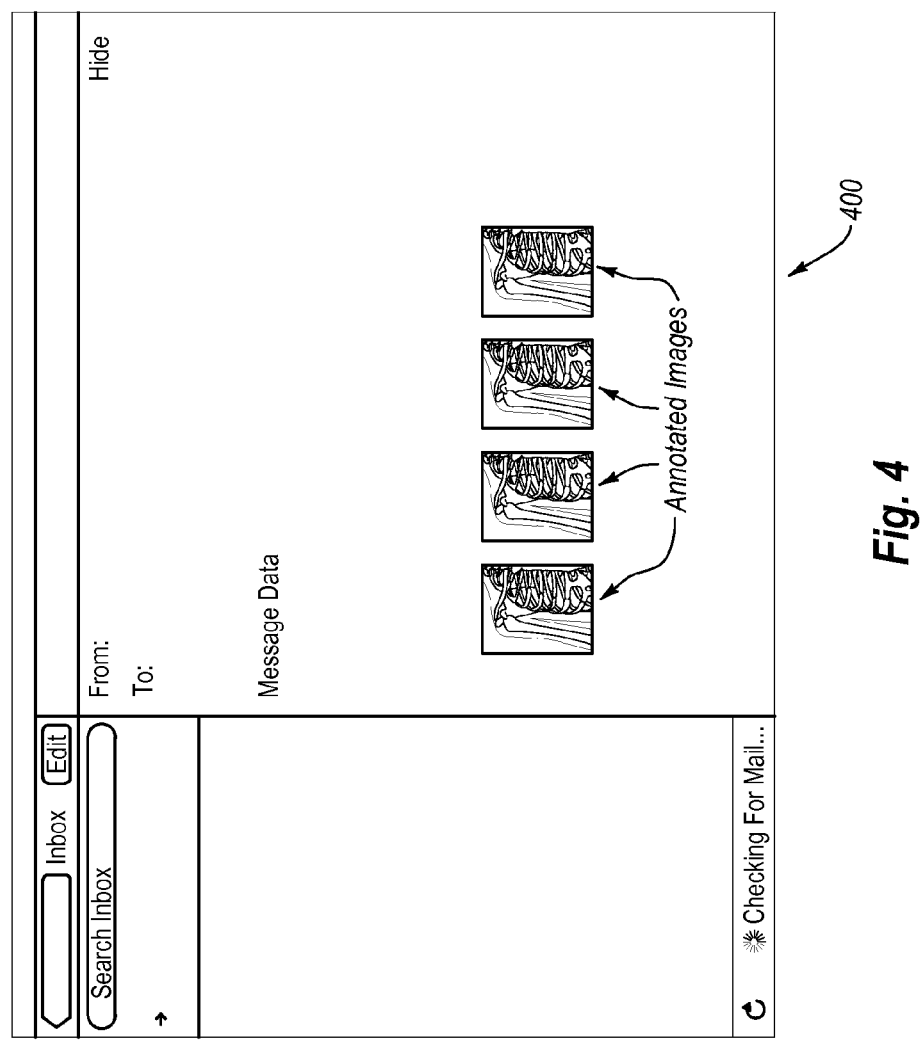
FIG. 4 illustrates a communications user interface 400 of an annotation system, in accordance with one or more implementations of the invention.

FIG. 4 illustrates a communications user interface 400 of the annotation system 104, in accordance with one or more implementations, with which a user can send records and graphical elements (annotated or un-annotated) to destination(s) 108 and/or the clearinghouse 106. As illustrated, the user can customize a message or other data that accompanies the records and/or graphical elements as they are sent. For instance, a doctor may customize a message to another doctor or a patient, or may make any other comments. This data can be stored and transmitted/accessed with the other image data (like X-rays) or other medical records associated with a patient. While FIG. 4 illustrates the composition of an e-mail message, the communications user interface 400 can, in other embodiments, send graphical elements in other forms (e.g., MMS, direct upload).

Returning briefly to FIG. 1, the clearinghouse 106 can comprise one or more computing systems configured to receive and make records, graphical images, etc., accessible to data sources 102, destinations 108, and the annotation system 104. As illustrated, the clearinghouse 106 can, in some embodiments, comprise a "cloud" configuration which includes one or more servers that are separated from the annotation system 104. Of course, one will appreciate that, in one or more implementations, the clearinghouse 106 may also be a part of the annotation system 104 itself. The clearinghouse 106 can employ any appropriate security and authentication mechanisms to protect any data stored therein from unauthorized access. Thus, communications between the clearinghouse 106 and any other component can be secured.

As discussed previously, the annotation environment 100 can be used to communicate graphical elements between a variety of sources and destinations in a variety of contexts beyond the medical field. For example, scientists can use the annotation environment 100 to share and annotate their research data. Furthermore, engineers can use the annotation environment 100 to share and annotate their designs. Still further, artists can use the annotation environment 100 to share and annotate their artwork. Accordingly, as mentioned previously, while some of the Figures illustrate implementations related to the medical field, the disclosure herein should not be viewed limiting the annotation environment 100 to use by the medical field.

Figure 5C:
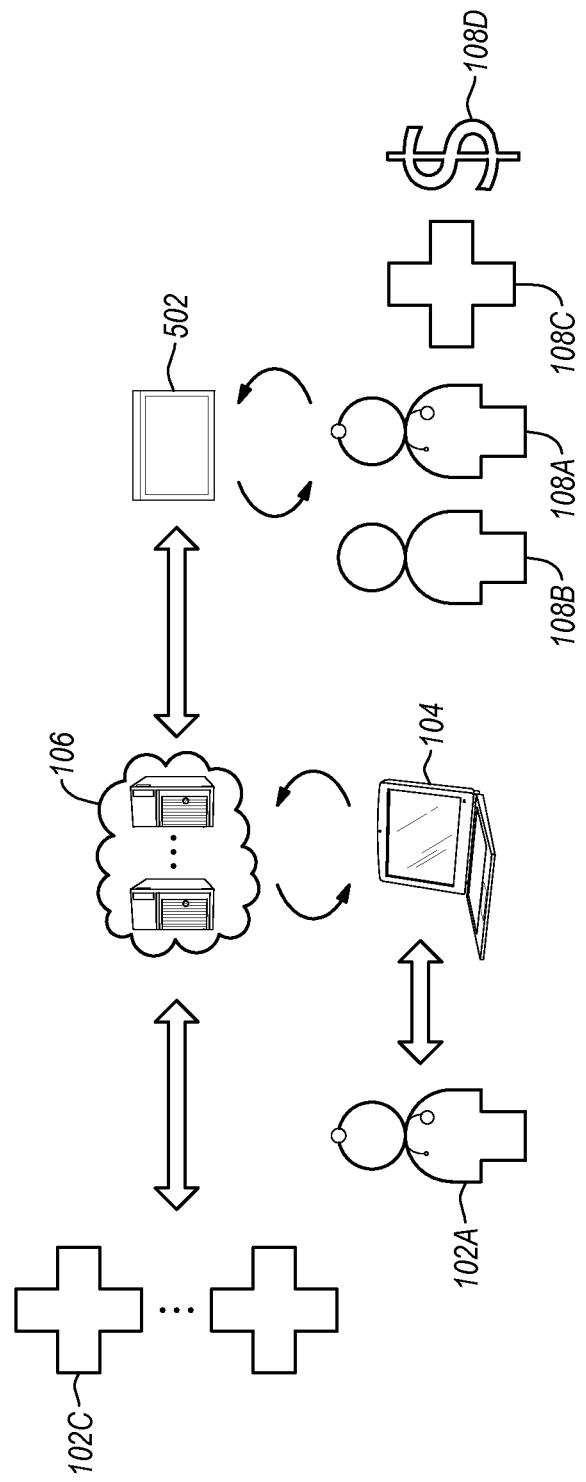
FIG. 5C illustrates a flow diagram of communication paths within an annotation environment, in accordance with one or more implementations of the invention.

Turning now to FIGS. 5A-5C, a plurality of flow diagrams are illustrated to reflect some of the communication paths that can be utilized within the annotation environment 100 in accordance with one or more implementations. The flow diagrams are for illustrative purposes only, and other communication paths are also possible. Each of the flow diagrams may use all or only a part of the illustrated annotation environment 100, as well as other components not previously discussed. For example, one or more implementations may include a web service 502 which may be provided in connection with, or separate from, the clearinghouse 106.

FIG. 5A, for example, illustrates an embodiment in which the annotation system 104 communicates directly with the data source(s) 102 and the destination(s) 108. In this embodiment, the annotation environment 100 may lack the clearinghouse 106, or the annotation system 104 may refrain from using the clearinghouse 106. Thus, a data source 102 (e.g., doctor 102A) may send one or more records and/or graphical elements directly to the annotation system 104.

As discussed previously, the annotation system 104 may acquire the graphical element(s) directly with an acquisition device (e.g., a camera 102E), or graphical element(s) may be sent to the annotation system 104 via a wireless 110A or a hard-wired 110B connection. After any appropriate annotations are made at the annotation system 104 (e.g., by the doctor 102A), the annotated graphical element(s) may be sent to a destination 108 (such as to a patient 108B). For example, the doctor 102A may use the communications user interface 400 at the annotation system 104 to send the annotated graphical element(s), along with any comments, to the patient 108B via e-mail, MMS, direct upload, etc.

FIG. 5B illustrates an additional embodiment in which the annotation system 104 communicates with the data source(s) 102 and the destination(s) 108 via a web service 502. For example, a doctor 102A may upload a patient's records and/or graphical elements to the web service 502. The annotation system 104, which is in communication with the web service 502, can receive the records and/or graphical elements. Then, the doctor 102A can make any appropriate changes (e.g., annotations) at the annotation system 104 and send these changes back to the web service 502. Subsequently, one or more destinations 108 can retrieve the records and/or graphical elements from the web service 502. Illustratively, the patient 108B, a different doctor 108A, a hospital 108C, or any other destination 108 can retrieve the records and/or graphical elements from the web service 502. Of course, similar to FIG. 5A, the data source(s) 102 and/or the destination(s) 108 may also be in direct communication with the annotation system 104. The web service 502 can be a standalone web service that is separated from the annotation system 104, or may be a component or module of the annotation system 104 or the clearinghouse 106.

FIG. 5C illustrates yet another embodiment in which the clearinghouse 106 is used to manage information from a variety of sources. For example, FIG. 5C illustrates that the clearinghouse 106 can be in communication with a plurality of hospitals 102C. Thus, the hospitals 102C can store a plurality of records and graphical elements for a plurality of patients. A doctor 102A can then use the annotation system 104 to retrieve medical records for a particular patient and to perform any appropriate annotations. The medical record, along with annotations, can then be synchronized back to the clearinghouse 106. A variety of destinations (e.g., doctors 108B, patients 108A, hospitals 108C, insurance companies 108D) can then retrieve the annotated records from the clearinghouse 106. This may be done directly, or via a separate web service 502 provided by the clearinghouse 106, as illustrated.

As indicated previously, particularly in the medical context, the foregoing annotation system may be used as part of a local or remote diagnosis and treatment system. For instance, some embodiments include mechanisms that enable a user to select anatomical regions of the human body from a displayed anatomical subassembly. From this selection, the user can be presented with information about corresponding conditions, the selection can be used to track medical conditions over time, or the selection can be used for annotation using the annotation system 104. Of course, the selection can be used for additional purposes beyond these examples.

Figure 6:
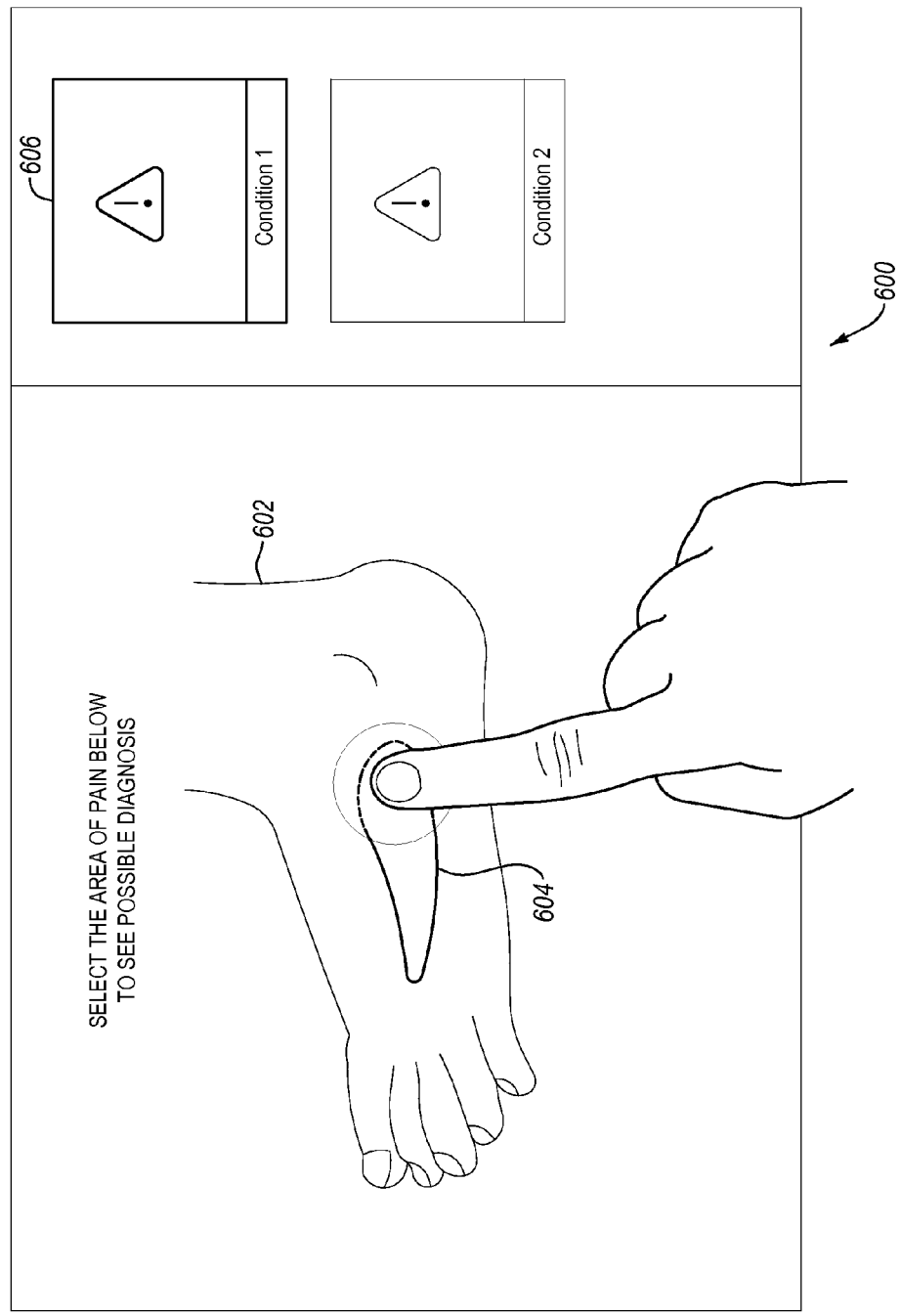
FIG. 6 illustrates a layout of an anatomical selection user interface, in accordance with one or more implementations of the invention.

FIG. 6 illustrates a layout of an anatomical selection user interface 600. As illustrated, a user (e.g., a patient, a doctor or other entity) may be presented with anatomical subassembly 602 representing an anatomical region of the human body (e.g., a human foot). From the anatomical subassembly 602, the user can select one more anatomical regions or elements (e.g. anatomical region 604), which can then be used for further processing or diagnosis, as described more fully below. As illustrated, for example, the user can be instructed to select an area in which pain is being experienced (i.e., "touch where it hurts"). This information can then be used by a doctor or by a computing system to determine possible conditions that may cause pain in the selected anatomical region 604. While the illustrated embodiment indicate that selection is based on experienced pain, selection can be based on any appropriate criteria, such as areas experiencing inflammation, areas of known injury, areas of discoloration or rash, areas of past treatment, etc.

The user may also be presented with one or more user interface elements (not illustrated) for identifying a relative measure of pain or perceived severity of a condition. Relative measures/magnitudes can be provided in any number of ways, such as through the selection of a number from a predefined range (e.g., 1-10), selection of a color from a color scale, selection of a graphical image of from a set of graphical images (e.g., a face selected from a set of faces having varying degrees of smiles and frowns), and so forth. Sets of objects having different sizes can also be selected from to reflect a relative magnitude. This information may be recorded as an annotation in the user's medical history (as a medical record), or may be used to further evaluate and provide information related to corresponding specialists, or even a diagnosis. In this manner, for example, it may be possible to interact with a virtual doctor's office and corresponding attendee.

The user may also be presented with a selection of specialists who are knowledgeable about the anatomical subassembly 602 and/or the condition. The selection of specialists can be local to the user's geographical area, or may include specialists from a broader geographical area. From the selection of specialists, the user can receive additional information about particular specialist(s) (e.g., cost, insurance affiliations, medical and educational credentials, contact information, photographs, reviews, hours of operation, and so forth). Further, the user can be presented with one or more options to contact the specialist directly. Thus, any relevant information about the user that has been gathered (e.g., the patient's medical history, the selected anatomical subassembly 602, the selected anatomical region 604, the indicated severity, patient-gathered photographs or records, patient-generated comments or annotations, doctor-gathered images or annotations) may be sent to a doctor (e.g., a specialist) for remote diagnosis, or for helping a doctor to remotely guide the user through an investigation of possible conditions (e.g., condition 606).

Similarly, when the user is a doctor, the gathered information (e.g., the selected region 604 and/or the severity) may be used for making annotations using the annotation system 104, for forming a diagnosis, for educating the patient about conditions that may correspond to the selection, for engaging other doctors, for tracking the patient's medical history, etc.

Figure 7:
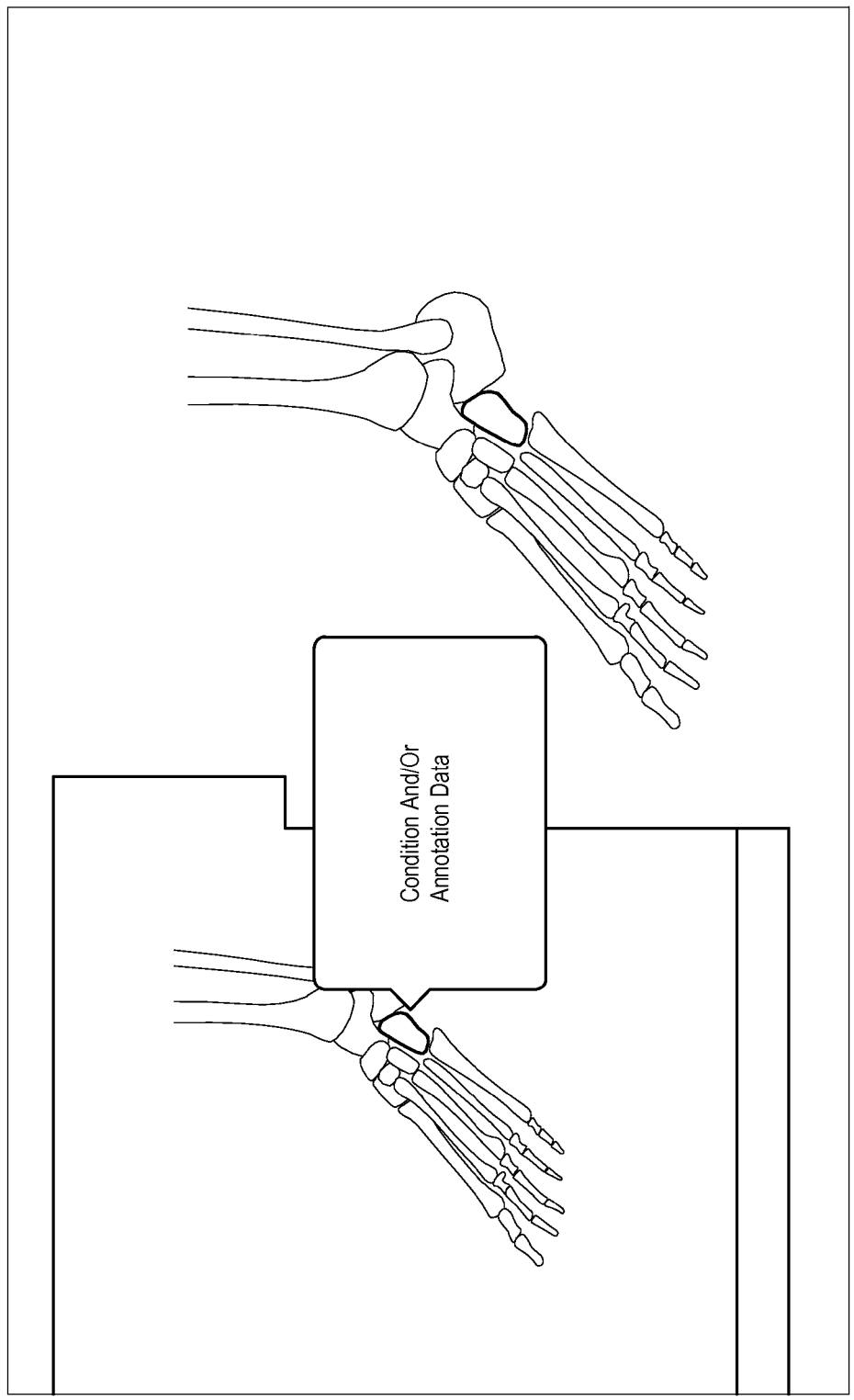
FIG. 7 illustrates a layout of a condition information user interface, in accordance with one or more implementations of the invention.

Once a user has selected an anatomical region 602, and a possible condition 606, further processing or diagnosis can include presenting the user with one or more corresponding condition information user interfaces. For example, FIG. 7 illustrates a layout of a condition information user interface 700 consistent with one or more implementations. The condition information user interface 700 can present information about the selected condition 606 in the form of photographs, audio and/or video presentations, illustrations, text, annotations and the like. Additionally or alternatively (not illustrated), the user can be presented with information about one or more medical specialists who have expertise with the selected condition (as discussed previously).

As mentioned, further processing or diagnosis can also include tracking a condition over time and/or annotating a medical record with the annotation system 104. For instance, after selecting an anatomical region 604, the selected region can be used as an aid in annotating a graphical element, such as a user or patient's X-Ray or MRI image. One will also appreciate that selection of an anatomical region can be made directly from the graphical element (e.g. from the user or patient's X-Ray or MRI image), or of from a simulated anatomical subassembly. Alternatively, selection of an anatomical region can be made on a simulated anatomical subassembly and then the selection can be transferred or overlaid on the displayed graphical element. However the selection is made, the selected anatomical region can be the basis of annotation, and this information can be saved (e.g. as a medical file at the clearinghouse 106) for future retrieval, or to maintain a record of the condition. For instance, a subsequent selection of the anatomical region 604, along with any annotations, can also be saved (e.g. at the clearinghouse 106) and/or can be compared to previously saved medical records.

Any display element (e.g., a graphical element being annotated, or the anatomical subassembly 602) can be displayed statically or dynamically. For instance, in some implementations, a user interface can enable a user to interactively rotate the display element in up to 360°, to selectively display descriptive annotations, to add or remove anatomical layers, to animate the displayed element through one or more types of motion, etc. Of course, the user interface can also display the display element dynamically without the use of user input as well.

Figure 8:
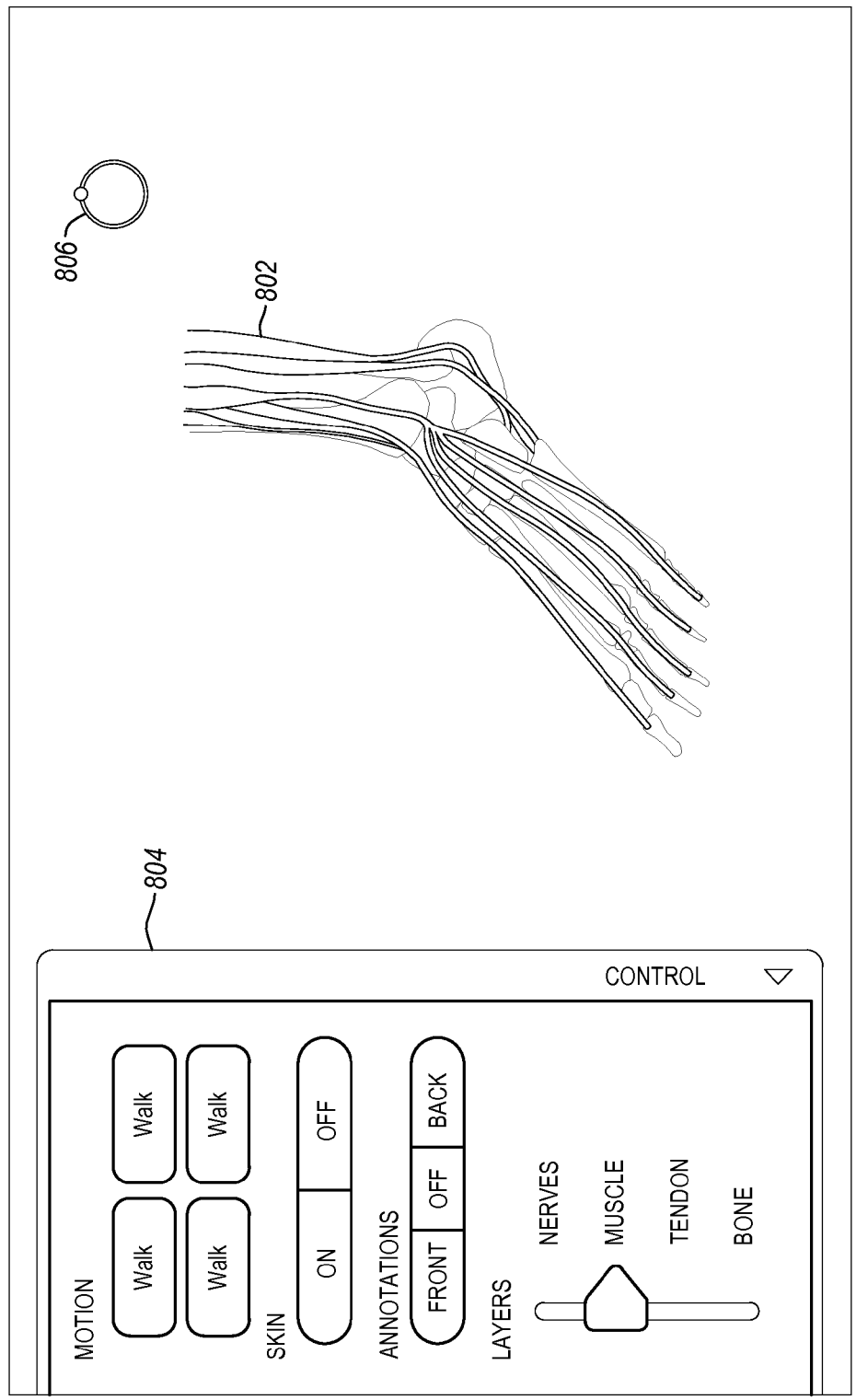
FIG. 8 illustrates a layout of a user interface which includes an interactive anatomical display, in accordance with one or more implementations of the invention.

FIG. 8 illustrates a layout of an interactive user interface 800 which includes an interactive anatomical display, according to one or more implementations. As shown, a user can interactively modify the display of an anatomical display element 802 using one or more interactive display options 804, one or more motion selectors 806, or input from a user input devices, etc. The interactive display options 804 can be used to selectively add or remove anatomical layers (e.g., nerves, muscle, tendon, bone), or to selectively add or remove annotations (e.g., anatomical labels).

The interactive display options 804 can be used to select a type of motion to apply to the display element 802. When selecting a "360°" motion option, the display element 802 can be automatically rotated, or selectively rotated based on user input. Once selected, the user may be able to click and/or drag on the display element 802 directly, or perform any other appropriate user input (e.g., using a separate user interface control. Other motions are also possible, such as motions that the display element 802 may actually perform (e.g., walking motion, ankle movement, and toe movement, etc.). In one or more embodiments, the user may use the motion selector 806 to perform the motion. The motion selector 806 can take any form appropriate to a motion type, such as buttons, sliders, switches, virtual or actual d-pads, virtual or actual joy-sticks, etc.

It will be appreciated that any of the text and any of the visual icons and objects displayed throughout the various user interfaces can be selectable links to initiate a function or to select the displayed item or a corresponding item, as generally described and inferred from the foregoing. In some instances, the user interfaces can be optimized for touch user interaction (e.g., via a tablet computer), while in others the application interfaces can be optimized for other types of user interaction, such is with pointer-based input devices.

It will also be appreciated that the selection of a region or element on an anatomical assembly or graphical element can include having a user make several selections through one or more related interfaces that allow a user to drill down from a first region, to a sub-region, to a specific element, for example. Any number or combination of menu selections may be made. The user can also make a selection from a pull-down menu that lists different elements/regions/features available for selection and/or make a selection of an element/region on an anatomical feature/assembly/subassembly, and so forth. Once a selection is made, it can be highlighted or otherwise visually modified to reflect the selection and to provide one or more interface elements for receiving and storing related annotations to the selected element(s) and/or for providing information related to the selected element(s).

FIGS. 1-8 provide a number of components, mechanisms, and user interfaces for annotating and sharing graphical elements, as well as components, mechanisms, and user interfaces for inputting information about medical conditions for diagnosis, education, tracking medical histories, etc. One or more disclosed implementations can enable rich, easy, and intuitive annotations, as well as flexible management and sharing of annotated graphical elements. One or more disclosed implementation can also enable remote diagnosis and/or guiding a user to information about a medical condition.

Figure 9:
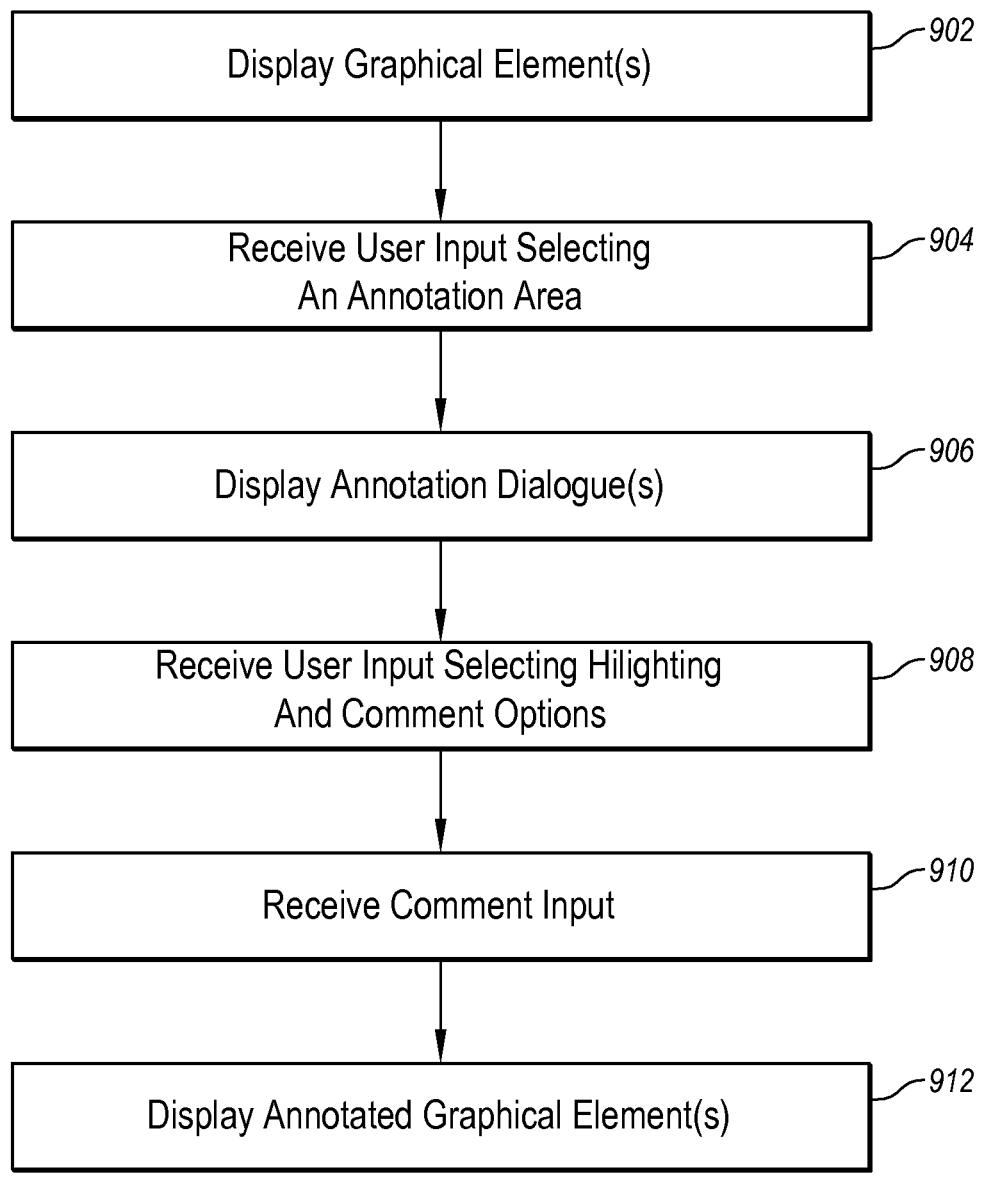
FIG. 9 illustrates a flowchart of a series of acts in a method, in accordance with an implementation of the present invention, for annotating a graphical element.
Figure 10:
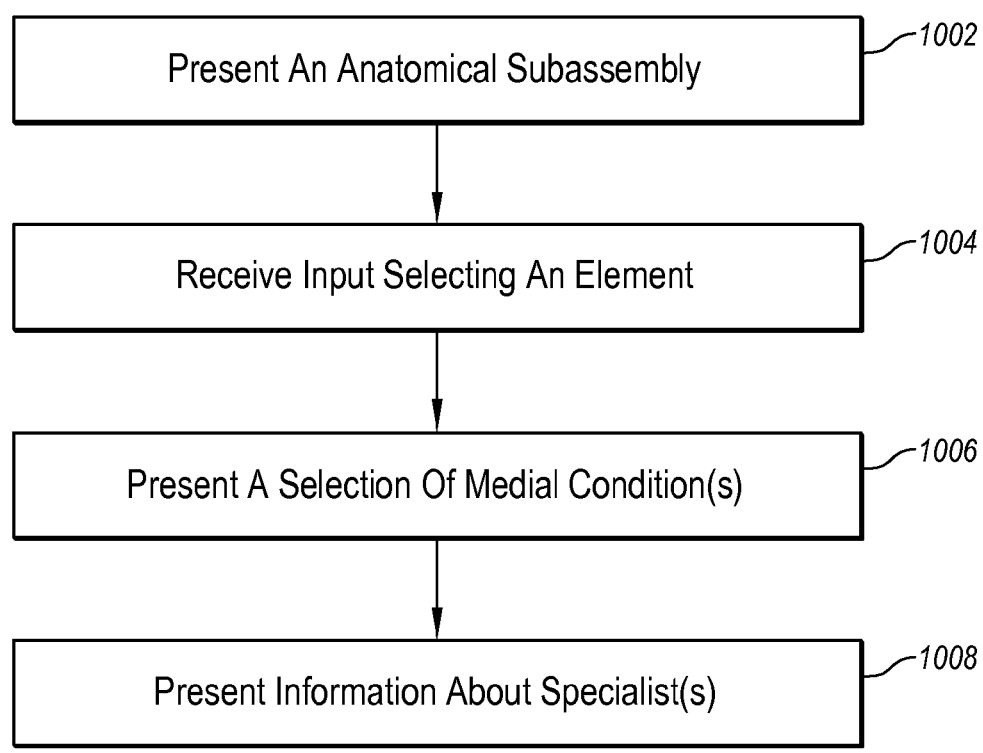
FIG. 10 illustrates a flowchart of a series of acts in a method, in accordance with an implementation of the present invention, for providing information about a medical condition based on user input.

Some implementations of the present invention can be described in terms of flowcharts comprising one or more acts in a method for accomplishing a particular result. Along these lines, FIGS. 9-10 illustrate flowcharts of computerized methods of annotating graphical elements and for selecting anatomical regions for further investigation. FIG. 9 illustrates a flowchart of a method for annotating a graphical element. FIG. 10 illustrates a flowchart of a method for providing information about a medical condition based on user input. The acts of FIGS. 9 and 10 are described herein below with respect to the schematics, diagrams, devices and components shown in FIGS. 1-8.

FIG. 9 shows that a method for annotating a graphical element can comprise an act 902 of displaying graphical element(s). Act 902 can include displaying one or more graphical elements at a user interface that includes one or more user-selectable annotation options for selecting one or more areas of the graphical elements for annotation. Act 902 can include the annotation user interface 300 displaying a graphical element, either statically or dynamically. The annotation user interface 300 can include any number of user-selectable graphical element manipulation options, such as color control options, cropping options, rotation options, drawing options, and so forth. The annotation user interface 300 can, in some embodiments, also employ a rich interactive display, such as the interactive user interface 800 of FIG. 8, which can add or remove layers to or from the graphical element, apply motion to the graphical element, rotate the graphical element in 360°, etc.

Act 902 can also include the annotation user interface 300 displaying one or more annotation interface controls 302. As discussed previously, the interface controls 302 can include one or more tools for selecting regions for annotation, tools for launching an annotation dialogue 304, and so forth. As shown, the displayed graphical element may be a medical or anatomical image, such as the illustrated human shoulder.

FIG. 9 also includes an act 904 of receiving user input selecting an annotation area. Act 904 can include receiving user input selecting one or more areas of the graphical elements for annotation. For example, act 904 can include the user selecting one or more regions of the graphical element by direct interaction with the graphical element (e.g., by directly clicking, touching, dragging, pinching, zooming, etc. on the graphical element). However, act 904 can also involve the use of selection tools, menus, buttons, etc. These tools may be provided as part of the interface controls 302, or as part of any other user interface element.

FIG. 9 also includes an act 906 of displaying annotation dialogue(s). Act 906 can include displaying an annotation dialogue which provides selection of one or more annotation options for annotating the selected one or more areas. The annotation dialogue can include one or more highlighting options, including one or more of shapes or colors. Of course, the annotation dialogue can include other highlighting options, such as images, animations, and so forth. Additionally, the annotation dialogue can include one or more comment input options, including one or more of text or audio input. Other comment options are also available, such as hand-drawing, video attachment or recording, etc.

After displaying the annotation dialogue(s), the illustrated method includes an act 908 of receiving user input selecting highlighting and comment options. Act 908 can include receiving user input selecting one or more of the highlighting options. For example, the user can select one or more shapes, colors, etc. from the annotation dialogue, or any other associated user interface controls. In some instances, the selected highlighting options include both a selection of shape (e.g., a circle) and a selection of color (e.g., red). When used in the medical context, selection of a shape can indicate a medical condition, and selection of a color can indicate a severity level of the medical condition.

Act 908 can also include receiving user input selecting one or more of the comment input options. Selecting a comment input option can include selecting a comment type (e.g., text, audio or video recording, handwriting, drawing, etc.). One will appreciate that the annotation dialogue 304 can include pre-selected highlighting and/or comment input options, and that comment input options can be selected by their mere use (e.g., a text comment type can be selected by the user beginning to enter text).

FIG. 9 also shows an act 910 of receiving comment input. Act 910 can include receiving user comment input and inputting at least one comment corresponding to the user comment input. For example, the user can type or otherwise enter text via the annotation dialogue, or an associated user interface control, using a physical or virtual keyboard. As illustrated, however, the user can also record audio and/or video comments. In such a circumstance, the act can include transcribing audio input into the at least one comment.

FIG. 9 also identifies an act 912 of displaying the annotated graphical element(s). This act can include displaying the one or more graphical elements along with the selected annotation, including the selected highlighting options and the inputted at least one comment. For example, once an annotation has been created, the annotation user interface 300 can display the graphical element along with any appropriate visual cues indicating that an annotation exists. When selected, the visual cue can be replaced or expanded to fully display any highlighting options and/or the entered comments.

Of course, the method can include any number of additional acts. For example, the method can also include an act of uploading the annotated graphical element(s) to a clearing house, or of sending the annotated graphical element(s) to a destination. In some embodiments, the method can include uploading the one or more graphical elements and the selected annotation as a medical file to a clearinghouse. The medical file can be accessed from the clearinghouse and displayed with a selectable graphical indicator of proximate areas of the selected annotation which, when selected, render the selected annotation. Rendering the selected annotation can comprise playing an audio comment, or playing a recorded video.

In addition to the foregoing, FIG. 10 illustrates that one or more additional implementations of providing information about a medical condition based on user input can comprise an act 1002 of presenting an anatomical subassembly. Act 1002 can include presenting a user with an anatomical subassembly representing an anatomical region of the human body, including one or more user-selectable display elements which, when selected, indicate one or more an areas in the anatomical subassembly representing areas in which a medical condition is experienced in the human body.

A user (e.g., a patient or a doctor) can be presented an anatomical subassembly 602 from which the user can select one or more anatomical regions or elements 604. In one or more embodiments, the medical condition can be pain experienced in the human body. Of course, the anatomical subassembly 602 can presented in any appropriate static or dynamic manner, and interactive tools can be provided, such as tools for rotating the anatomical subassembly to provide a 360° view of the anatomical subassembly 602.

FIG. 10 illustrates that embodiments of the invention also include an act 1004 of receiving input selecting a display element, such as, for example, input selecting one or more of the user-selectable elements of the anatomical assembly. In one embodiment, the user touches or clicks on anatomical region/element 604 to select that region/element of the anatomical subassembly 602. This selection can also include presenting the user with other options for providing additional information about the selection. For example, the act of selecting can include presenting the user with one or more user-selectable interface elements for further selecting a severity level (e.g., a pain level) associated with the experience medical condition.

FIG. 10 includes an act 1006 of presenting a selection of medical condition(s) to a user, such as a selection of one or more medical conditions corresponding to the one or more selected elements of the anatomical subassembly, wherein the one or more medical conditions are medical conditions corresponding to the one or more selected elements of the anatomical assembly. This can also include presenting the user with a list or menu of medical conditions that may apply to the selected anatomical subassembly 602. From this list, the user can select one or more of the medical conditions (e.g., medical condition 606). Then, the user can be presented with information about the selected medical condition(s). Illustratively, the user may be presented with a condition information user interface 700 which provides textual, visual, and/or audio information about the selected condition. The condition information user interface 700 can also provide information about procedures for treating the one or more medical conditions.

FIG. 10 also includes an act 1008 of presenting information about specialists. Act 1008 can include presenting the user with information about one or more medical specialists corresponding to one or more of the medical conditions, as well as the one or more selected elements of the anatomical subassembly. For example, when the user is a patient, the patient can send any gathered information and any user annotations to a specialist for remote diagnosis. Alternatively, when the user is a doctor, the user can send the information to another doctor for advice, additional opinions, etc.

It will be appreciated that the method can also comprise annotation by the annotation system 104. Thus, at any point, the user can be presented with one or more user-selectable annotation options for selecting one or more areas of the anatomical subassembly 602 for annotation. After annotations are made, these annotations can be uploaded as a medical file to a clearinghouse where they can be made accessible to doctors, patients, insurance companies, hospitals, etc.

Accordingly, FIGS. 1-10 provide a number of components and mechanisms for annotating graphical element and for providing medical information or assistance based on selected graphical elements. One or more disclosed implementations also provide for a central clearinghouse for sharing graphical elements between annotation systems, data sources, and destinations.

The foregoing embodiments may be also practiced by a computer system including any number of one or more processors and computer readable media such as computer memory or other storage media which is detachable from the processor(s). In particular, the computer memory may store computer executable instructions that when executed by one or more processors cause various functions to be performed.

Embodiments may also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer readable storage media and transmission computer readable media.

Physical computer readable storage media (device(s)) includes RAM, ROM, EEPROM, CD-ROM or other optical disk storage (such as CDs, DVDs, etc), magnetic disk storage or other magnetic storage devices, flash memory, thumb drives, portable memory drives, solid state disks, or any other physical medium which can be used to store desired program code means in the form of computer-executable instructions or data structures and which can be accessed by a general purpose or special purpose computer. The storage devices do not consist of merely transitory carrier waves and/or merely transitory signals.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer readable media to physical computer readable storage media (or vice-versa). For example, computer-executable instructions or data structures received over a network or data link can be buffered in RAM within a network interface card or module (e.g., a "NIC"), and then eventually transferred to computer system RAM and/or to less volatile computer readable physical storage media at a computer system. Thus, computer readable physical storage media can be included in computer system components that also (or even primarily) utilize transmission media.

Computer-executable instructions comprise, for example, instructions and data which cause a general purpose computer, special purpose computer, or special purpose processing device (e.g., CPU device(s)) to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, tablet computers (e.g., iPads, Android tablets), message processors, hand-held devices (e.g., iPods), multi-processor systems, microprocessor-based or programmable consumer electronics, network PCs, minicomputers, mainframe computers, mobile telephones, PDAs, other smart devices, or other interactive display devices or personal computers, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. One or more hardware storage devices having stored thereon computer executable instructions that, when executed by one or more processors of a computer system, implement a method for annotating a graphical element, the method comprising:
   displaying one or more graphical elements at a user interface, the one or more graphical elements representing one or more anatomical structures;
   simultaneous to display of the one or more graphical elements, displaying a user-selectable annotation button that, when selected, enables specification one or more points of the one or more graphical elements for annotation;
   receiving user input selecting the annotation button;
   subsequent to receiving the user input selecting the annotation button, receiving user input specifying a particular point of the one or more graphical elements for entry of an annotation;
   subsequent to receiving the user input specifying the particular point of the one or more graphical elements for entry of an annotation, displaying an annotation dialogue that provides selection of a plurality of annotation options for annotating the specified particular point, the annotation dialogue being visually associated with the specified particular point of the one or more graphical elements, the annotation dialogue including:
      one or more highlighting options for visually emphasizing the specified particular point, including one or more of shapes or colors; and
      one or more comment input options for providing information relevant to the specified particular point, including one or more of text or audio input;
   receiving user input selecting one or more of the highlighting options and one or more of the comment input options;
   receiving user comment input that provides at least one comment corresponding to the user comment input; and
   displaying the one or more graphical elements along with the selected annotation, including the selected highlighting options and the inputted at least one comment.

2. The one or more hardware storage devices of claim 1, wherein the selected highlighting options include both a selection of shape and a selection of color.

3. The one or more hardware storage devices of claim 2, wherein the selection of shape indicates a medical condition, and wherein the selection of color indicates a severity level of the medical condition.

4. The one or more hardware storage devices of claim 1, wherein the user interface further includes one or more user-selectable graphical element manipulation options, including one or more of a color control option, a cropping option, a rotation option, or a drawing option.

5. The one or more hardware storage devices of claim 1, wherein the user comment input comprises audio input, the method further comprising:
   automatically transcribing the audio input into the at least one comment.

6. The one or more hardware storage devices of claim 1, further comprising:
   uploading the one or more graphical elements and the selected annotation as a medical file to a clearinghouse.

7. The one or more hardware storage devices of claim 6, wherein the medical file is accessed from the clearinghouse and displayed with a selectable graphical indicator of proximate areas of the selected annotation which, when selected, render the selected annotation.

8. The one or more hardware storage devices of claim 7, wherein rendering the selected annotation comprises playing an audio comment.

9. The one or more hardware storage devices of claim 1, wherein displaying one or more graphical elements at the user interface comprises overlaying a virtual model over an image.

10. A method, implemented at a computer system that includes one or more processors, for annotating a graphical element, the method comprising:
   displaying one or more graphical elements at a user interface, the one or more graphical elements representing one or more anatomical structures;
   simultaneous to display of the one or more graphical elements, displaying a user-selectable annotation button that, when selected, enables specification one or more points of the one or more graphical elements for annotation;
   receiving user input selecting the annotation button;
   subsequent to receiving the user input selecting the annotation button, receiving user input specifying a particular point of the one or more graphical elements for entry of an annotation;
   subsequent to receiving the user input specifying the particular point of the one or more graphical elements for entry of an annotation, displaying an annotation dialogue that provides selection of a plurality of annotation options for annotating the specified particular point, the annotation dialogue being visually associated with the specified particular point of the one or more graphical elements, the annotation dialogue including:
      one or more highlighting options for visually emphasizing the specified particular point, including one or more of shapes or colors; and
      one or more comment input options for providing information relevant to the specified particular point, including one or more of text or audio input;
   receiving user input selecting one or more of the highlighting options and one or more of the comment input options;
   receiving user comment input that provides at least one comment corresponding to the user comment input; and
   displaying the one or more graphical elements along with the selected annotation, including the selected highlighting options and the inputted at least one comment.

11. The method of claim 10, wherein the selected highlighting options include both a selection of shape and a selection of color.

12. The method of claim 11, wherein the selection of shape indicates a medical condition, and wherein the selection of color indicates a severity level of the medical condition.

13. The method of claim 10, wherein the user interface further includes one or more user-selectable graphical element manipulation options, including one or more of a color control option, a cropping option, a rotation option, or a drawing option.

14. The method of claim 10, wherein the user comment input comprises audio input, the method further comprising:
   automatically transcribing the audio input into the at least one comment.

15. The method of claim 10, further comprising:
   uploading the one or more graphical elements and the selected annotation as a medical file to a clearinghouse.

16. The method of claim 15, wherein the medical file is accessed from the clearinghouse and displayed with a selectable graphical indicator of proximate areas of the selected annotation which, when selected, render the selected annotation.

17. The method of claim 16, wherein rendering the selected annotation comprises playing an audio comment.

18. The method of claim 10, wherein displaying one or more graphical elements at the user interface comprises overlaying a virtual model over an image.

19. A computer system, comprising:
   one or more hardware processors; and
   one or more hardware storage devices having stored thereon computer-executable instructions that, when executed by the one or more hardware processors, cause the computer system to provide a user interface for annotating a graphical element, including the following:
      displaying one or more graphical elements at a user interface, the one or more graphical elements representing one or more anatomical structures;
      simultaneous to display of the one or more graphical elements, displaying a user-selectable annotation button that, when selected, enables specification one or more points of the one or more graphical elements for annotation;
      receiving user input selecting the annotation button;
      subsequent to receiving the user input selecting the annotation button, receiving user input specifying a particular point of the one or more graphical elements for entry of an annotation;
      subsequent to receiving the user input specifying the particular point of the one or more graphical elements for entry of an annotation, displaying an annotation dialogue that provides selection of a plurality of annotation options for annotating the specified particular point, the annotation dialogue being visually associated with the specified particular point of the one or more graphical elements, the annotation dialogue including:
         one or more highlighting options for visually emphasizing the specified particular point, including one or more of shapes or colors; and
         one or more comment input options for providing information relevant to the specified particular point, including one or more of text or audio input;
      receiving user input selecting one or more of the highlighting options and one or more of the comment input options;
      receiving user comment input that provides at least one comment corresponding to the user comment input; and
      displaying the one or more graphical elements along with the selected annotation, including the selected highlighting options and the inputted at least one comment.

20. The computer system of claim 19 further comprising:
   uploading the one or more graphical elements and the selected annotation as a medical file to a clearinghouse.

* * * * *